United States Patent
Zetlmeisl et al.

(10) Patent No.: US 9,719,035 B2
(45) Date of Patent: Aug. 1, 2017

(54) METHOD AND COMPOSITIONS FOR INHIBITION OF NAPHTHENIC ACID INDUCED CORROSION

(71) Applicant: Baker Hughes Incorporated, Houston, TX (US)

(72) Inventors: Michael J. Zetlmeisl, St. Louis, MO (US); Bradley G. Harrell, Pearland, TX (US); Bradley G. Borgard, Cedar Park, TX (US); Scott Bieber, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 13/925,535

(22) Filed: Jun. 24, 2013

(65) Prior Publication Data
US 2015/0376516 A1    Dec. 31, 2015

Related U.S. Application Data

(63) Continuation of application No. 11/601,401, filed on Nov. 17, 2006, now abandoned.

(60) Provisional application No. 60/818,086, filed on Jun. 30, 2006.

(51) Int. Cl.
| | |
|---|---|
| *C10G 75/02* | (2006.01) |
| *C07C 7/20* | (2006.01) |
| *C10G 7/10* | (2006.01) |
| *C09K 15/12* | (2006.01) |
| *C09K 15/30* | (2006.01) |

(52) U.S. Cl.
CPC ............... *C10G 75/02* (2013.01); *C07C 7/20* (2013.01); *C09K 15/12* (2013.01); *C09K 15/30* (2013.01); *C10G 7/10* (2013.01); *C10G 2300/203* (2013.01); *C10G 2300/4075* (2013.01)

(58) Field of Classification Search
CPC ...................................................... C10G 75/02
See application file for complete search history.

(56) References Cited

U.S. PATENT DOCUMENTS

| | | | | |
|---|---|---|---|---|
| 4,339,349 A | * | 7/1982 | Martin | C23F 11/10 422/12 |
| 4,446,056 A | * | 5/1984 | Thompson | C07D 211/82 252/391 |
| 5,863,415 A | * | 1/1999 | Zetlmeisl | C07F 9/1651 208/47 |

FOREIGN PATENT DOCUMENTS

| | | | | |
|---|---|---|---|---|
| JP | 55-102506 | * | 8/1980 | ............. A01N 43/82 |

OTHER PUBLICATIONS

Derwent English Abstract of JP 55-102506, no date.*

* cited by examiner

*Primary Examiner* — Renee Robinson
(74) *Attorney, Agent, or Firm* — Mossman, Kumar & Tyler, P.C.

(57) ABSTRACT

Corrosion induced by the presence of naphthenic acids in hydrocarbon fluids, particularly where such fluids are at elevated temperatures, may be inhibited or controlled through use of corrosion inhibiting compositions comprising a combination of a minor portion of a phosphorus-based constituent and a major portion of a sulfur-based constituent, nitrogen-based constituent, or combination thereof. In another embodiment the sulfur-based constituent and/or nitrogen-based constituent may be used without any phosphorus-based constituent. Where the compounds are appropriately selected, the compositions may inhibit corrosion to a degree comparable or nearly comparable to the inhibition provided by an equal amount of some conventional phosphorus-based compounds alone, but are significantly less likely to impair catalyst activity in downstream cracking and refinery operations.

8 Claims, No Drawings

METHOD AND COMPOSITIONS FOR INHIBITION OF NAPHTHENIC ACID INDUCED CORROSION

CROSS-REFERENCE TO A RELATED APPLICATION

This application claims the benefit of U.S. Provisional Application No. 60/818,086, filed Jun. 30, 2006.

BACKGROUND OF THE INVENTION

1. Field of the Invention

This invention relates to controlling corrosion in acidic hot hydrocarbons. More particularly, this invention relates to compositions and methods for inhibiting naphthenic acids induced corrosion of iron-containing metal alloys in hot hydrocarbons.

2. Background Art

It is widely known in the art that the processing of crude oil in its various fractions may lead to damage of iron-containing metal surfaces of the processing equipment. This corrosion is frequently associated with, in particular, the presence and activity of naphthenic acids. The corrosion occurs when the amount of naphthenic acids in the hydrocarbon reaches some critical value indicated by total acid number ("TAN"), expressed as milligrams of potassium hydroxide required to neutralize the acids in a one-gram sample. Older literature uses a rule of thumb that a TAN greater than 0.5 is required for a crude oil to cause naphthenic acid corrosion, but more recent experience indicates that the critical value can vary considerably from this value. When elevated temperatures are applied to the crude, such as the 175° C. (–347° F.) to about 400° C. (–752° F.) temperatures customarily used to refine and distill the oil, the corrosion problem is typically further exacerbated.

While various corrosion inhibitors are known in the art, the efficacy of any particular corrosion inhibitor is generally known to be dependent upon the circumstances under which it is used. As a result, a variety of corrosion inhibitors have been developed and targeted for use for treating particular crudes, for protecting particular metals, for inhibiting specific types of corrosion, and/or for use under particular conditions of temperature, environment, and the like. For example, U.S. Pat. No. 3,909,447 describes certain corrosion inhibitors as useful against corrosion in relatively low temperature oxygenated aqueous systems, such as water floods, cooling towers, drilling muds, air drilling and auto radiator systems. That patent also notes that many corrosion inhibitors capable of performing in non-aqueous systems and/or non-oxygenated systems perform poorly in aqueous and/or oxygenated systems. The reverse is true as well. The fact that an inhibitor that has shown efficacy in oxygenated aqueous systems does not suggest that it would show efficacy in a hydrocarbon. Moreover, the fact that an inhibitor has been effective at relatively low temperatures does not indicate that it would also be effective at elevated temperatures. In fact, it is common for inhibitors that are very effective at relatively low temperatures to become ineffective at temperatures such as the 175° C. (–347° F.) to 400° C. (–752° F.) temperatures encountered in oil refining. At such temperatures, corrosion is notoriously troublesome and difficult to alleviate. Thus, U.S. Pat. No. 3,909,447 contains no teaching or suggestion that it would be effective in non-aqueous systems such as hydrocarbon fluids, especially hot hydrocarbon fluids, nor is there any indication in that patent that the compounds disclosed therein would be effective against naphthenic acid induced corrosion at elevated temperatures.

As commonly used, naphthenic acid is a collective term for certain organic acids present in various crude oils. Although minor amounts of other organic acids may also be present, it is understood that the majority of the acids in a naphthenic acid based crude are naphthenic in character, i.e., with a saturated ring structure that conforms to a formula such as one of the following:

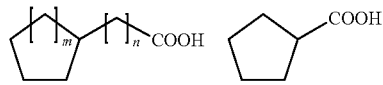

In the above formulas, m is typically 1-2, and n varies. It is basically any carboxylic acid group with at least one saturated 5 or 6 membered ring attached. One simple example is cyclopentanoic acid.

The molecular weight of naphthenic acid can extend over a large range. However, the majority of the naphthenic acid in crude oils is found, after distilling, in the lighter fractions, including, for example, gas oil. When hydrocarbons containing such naphthenic acid contact iron-containing metals, especially at elevated temperatures, severe corrosion problems arise.

Various approaches to controlling naphthenic acid induced corrosion have included neutralizing and/or removing the naphthenic acids from the crude being processed; blending low acid number oils with more corrosive high acid number oils to reduce the overall neutralization number; and using relatively expensive corrosion-resistant alloys in the construction of the crude's processing apparatus. These attempts are generally disadvantageous in that they require additional processing and/or add substantial cost to treatment of the crude oil. Alternatively, U.S. Pat. No. 4,443,609 discloses certain tetrahydrothiazole phosphonic acids and esters as being useful additives for inhibiting acid corrosion. Such inhibitors can be prepared by reacting certain 2,5-dihydrothiazoles with a dialkyl phosphite. While these tetrahydrothiazoles phosphonic acids or esters offer good corrosion inhibition, they tend to break down under high temperature conditions.

Another disadvantage to using phosphorus-based compounds as corrosion inhibitors is that the phosphorus has been alleged to impair the function of various catalysts used to treat crude oil, such as in fixed-bed hydrotreaters and hydrocracking units. Thus, crude oil processors are often faced with a dilemma, since corrosion itself, if not inhibited, may result in accumulation in the hydrocarbon fluid of a catalyst-impairing amount of iron, as high as 10 to 20 ppm in some cases. Unfortunately, while there are a number of commercially available non-phosphorus-based inhibitors, they are known to be generally somewhat less effective than the phosphorus-based compounds.

A significant advance in phosphorus-based naphthenic acid induced corrosion inhibitors is reported in U.S. Pat. No. 4,941,994. Therein it is disclosed that metal corrosion in hot acidic liquid hydrocarbons in inhibited by the presence of a corrosion inhibiting amount of a dialkyl and/or trialkyl phosphite with an optional thiazoline. Another patent, U.S. Pat. No. 5,863,415, discloses that thiophosphorus compounds of a specific formula are particularly useful for corrosion inhibition in hot liquid hydrocarbons and may be used at concentrations that add to the fluid less of the catalyst-impairing phosphorus than some of the previous phosphorus-based corrosion inhibitors. These thiophosphorus compounds also offer the advantage of being able to be prepared from relatively low cost starting materials.

In view of the above, it would be desirable in the art to find additional methods and compositions for inhibiting or controlling naphthenic acid induced corrosion in crude oils, particularly at elevated temperatures, that do not suffer from the drawbacks of the prior art.

SUMMARY OF THE INVENTION

Accordingly, a method for inhibiting naphthenic acid corrosion of metals in hydrocarbon fluids has been found, comprising adding to a hydrocarbon fluid, in an amount sufficient to inhibit corrosion therein, an inhibitor composition comprising a phosphorus-based constituent comprising at least one compound selected from the group consisting of: (a) thiophosphorus compounds conforming to the formula

FORMULA 1

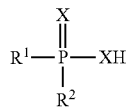

wherein $R^1$ is $R^3(OCH_2CH_2)_n$ or $R^3(OCH_2CH_2)_nO$; $R^2$ is the same as $R^1$ or XH, each X being independently sulfur or oxygen; provided however that at least one X is sulfur; $R^3$ is an alkyl group of from about 6 to about 18 carbon atoms; and n is an integer of from about 0 to about 12; (b) salts of the thiophosphorus compounds; (c) alkyl and aryl esters of the thiophosphorus compounds; (d) isomers of the thiophosphorus compounds; and (e) phosphate esters; and a second constituent selected from a sulfur-based constituent comprising at least one compound conforming to one of the following formulas:

FORMULA 2

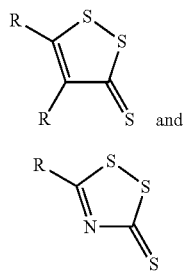

and

FORMULA 3

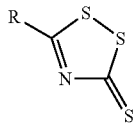

wherein R is independently —H, —SH, —SR, —SSR, or C1-C12 normal or partially or fully branched alkyl that is saturated or unsaturated; a nitrogen-based constituent comprising at least one compound conforming to one of the following formulas:

FORMULA 4

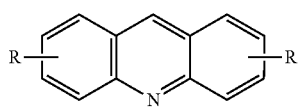

FORMULA 5

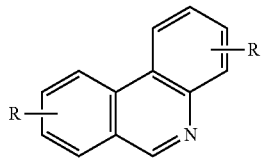

FORMULA 6

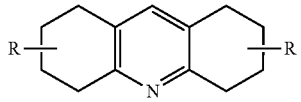

FORMULA 7

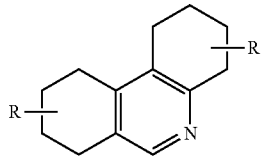

FORMULA 8

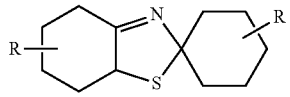

wherein R is independently —H, —SH, —SR, —SSR, or C1-C12 normal or partially or fully branched alkyl that is saturated or unsaturated; and combinations thereof; provided that the phosphorus-based constituent is present in minor portion.

The invention further includes compositions for inhibiting or controlling naphthenic acid induced corrosion in a hydrocarbon fluid comprising a phosphorus-based constituent comprising at least one compound as defined hereinabove and a second constituent selected from a sulfur-based constituent comprising at least one compound as defined hereinabove; a nitrogen-based constituent comprising at least one compound as defined hereinabove; and combinations thereof; provided that the phosphorus-based constituent is in minor portion and the sulfur-based constituent, nitrogen-based constituent, or combination thereof is in major portion.

The invention still further includes a method for inhibiting naphthenic acid corrosion of metals in hydrocarbon fluids, comprising adding to a hydrocarbon fluid, in an amount sufficient to inhibit corrosion therein, an inhibitor composition comprising a sulfur-based constituent as defined hereinabove; a nitrogen-based constituent as defined hereinabove; or a combination thereof; provided that the sulfur-based constituent, the nitrogen-based constituent, or combination thereof is present in major portion.

DETAILED DESCRIPTION OF THE INVENTION

The several advantages achieved by the present invention include stability of the inhibitor composition at high temperatures and, surprisingly, capability to achieve comparable or near-comparable corrosion inhibition, when a given total amount of the inventive inhibitor composition is compared with using, for example, a thiophosphorus compound or phosphate ester alone. This means that, by including only a minor proportion of the phosphorus-based compound along with a major proportion of a sulfur-based compound such as tropylene and/or a nitrogen-based compound, the problems associated with adding phosphorus, such as catalyst impairment, can be avoided or greatly mitigated, while still achieving excellent inhibition of naphthenic acid induced corrosion in hydrocarbon fluids, particularly at high temperatures. In other, non-limiting embodiments, either the sulfur-based compound or the nitrogen-based compound may be used alone or in combination with each other, without the use of any phosphorus-based compound.

The hydrocarbon fluids of particular interest in this invention are those fractions formed during crude oil refining processes. Such include, in one non-limiting embodiment, those that include, at least in part, gas oils and light lubricating oils. These hydrocarbon fluids are typically heated to a temperature in the range of from about 175° C. to about 400° C., and more particularly from about 205° C. to about 400° C. At these temperatures naphthenic acid induced corrosion, as well as corrosion attributable to other similar organic acids or phenols such as cresylic acid, particularly in these lighter fractions, is extremely aggressive and difficult to inhibit. The method and compositions of the present invention are particularly suited to such non-aqueous liquids and to protection of iron-containing metal surfaces.

In order to inhibit the corrosion in such hot hydrocarbon fluids, the compositions of the invention are typically added to the fluid. The fluid may be still cool or already heating or heated. In other non-limiting embodiments the stream may be previously treated or otherwise converted, and as such may form, for example, the feed to a distillation unit or reactor.

The inventive corrosion inhibitor compositions have, in one non-limiting embodiment, at least two distinct constituents. Of these, a major portion comprises at least one sulfur-based compound, or one nitrogen-based compound, or a combination thereof. As used herein, the term "major portion" is defined to mean more than about 50 percent and, in some non-limiting embodiments, it is at least about 60 percent; and in other non-limiting embodiments, it is at least about 75 percent; and in still other non-limiting embodiments, it is at least about 85 percent; by weight based on the total inhibitor composition.

The sulfur-based constituent is defined as comprising at least one compound conforming to one of the following formulas:

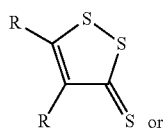

FORMULA 2 or

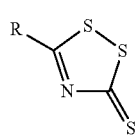

FORMULA 3 wherein R is independently —H, —SH, —SR, —SSR or C1-C12 normal or partially or fully branched alkyl that is saturated or unsaturated.

Some non-limiting examples of such sulfur-based compound include tropylene (1,2-dithiole-3-thione), which conforms to

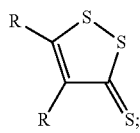

FORMULA 2

1,2,4-dithiazole-3-thione, which conforms to

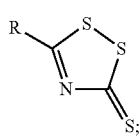

FORMULA 3 combinations thereof; and the like.

In some non-limiting embodiments the second constituent of the novel inhibitor compositions may be nitrogen-based. This constituent comprises a compound conforming to one of the following formulas:

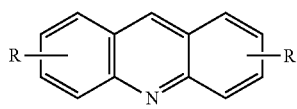

FORMULA 4

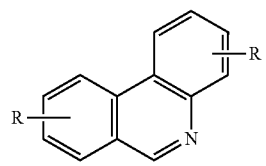

FORMULA 5

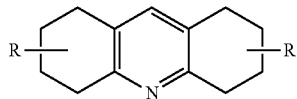

FORMULA 6

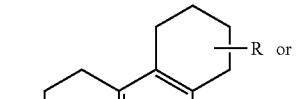

FORMULA 7

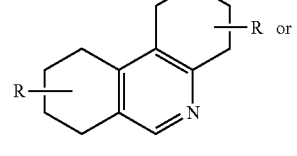

FORMULA 8 wherein R is independently —H, —SH, —SR, —SSR, or C1-C12 normal or partially or fully branched alkyl that is saturated or unsaturated.

Non-limiting examples of nitrogen-based compounds include, in general, phenanthridines and acridines. Non-limiting examples of these include acridine, phenanthridine, octahydroacridine (OHA), octahydrophanthridine (OHP), 1,3-thiazole, combinations thereof, and the like.

In some non-limiting embodiments of the present invention, either the sulfur-based constituent, or the nitrogen-based constituent, or a combination thereof, may be employed as the sole or primary constituent of the corrosion inhibitor composition, i.e., this constituent is present in major portion. In other non-limiting embodiments, either of these categories of compounds may be included, alone or together, in a composition including a phosphorus-based constituent, provided that the nitrogen-based constituent is present, in total, in minor portion in the overall inhibitor composition.

As used herein, the term "minor portion" is defined to mean less than about 50 percent of the total inhibitor composition. In some non-limiting embodiments it is less than about 40 percent; in other non-limiting embodiments it is less than about 25 percent; and in still other non-limiting embodiments it is less than about 15 percent; by weight based on the total inhibitor composition. The phosphorus-based compound, or compounds, are selected from the group consisting of (a) thiophosphorus compounds of FORMULA 1 wherein $R^1$ is $R^3(OCH_2CH_2)_n$ or $R^3(OCH_2CH_2)_nO$; $R^2$ is the same as $R^1$ or XH, each X being independently sulfur or oxygen; provided however that at least one X is sulfur; $R^3$ is an alkyl group of from about 6 to about 19 carbon atoms; and n is an integer of from about 0 to about 12; (b) salts of the thiophosphorus compounds; (c) alkyl and aryl esters of the thiophosphorus compounds; (d) isomers of the thiophosphorus compounds; and (e) phosphate esters. The inhibitor composition may include just one of the above phosphorus-based compounds, or any combination thereof, provided that, when included, the total of these compounds remains a minor portion, as that term is defined hereinabove, of the corrosion inhibitor composition as a whole.

For example, in certain non-limiting embodiments a selected thiophosphorus compound may be an alkyl dithiophosphonic acid of FORMULA 1 wherein $R^1$ and $R^2$ are each $R^3(OCH_2CH_2)_nO$, each X is sulfur, $R^3$ is an alkyl group of about 8 to about 10 carbon atoms, and n is an integer from about 3 to about 5. In another non-limiting embodiment, two compounds may be selected, in one of which $R^1$ is $R^3(OCH_2CH_2)_nO$, and in the other of which $R^1$ is $R^3(OCH_2CH_2)_n$. In the present invention, wherever more than one component, e.g., one or more compound or combination of compounds, is selected, such may be added to the hydrocarbon feed or stream in separate doses or they may be combined into an additive composition prior to their addition. In still another non-limiting embodiment, a thiophosphorus compound may be included along with an isomer thereof and/or with a phosphate ester. In yet another non-limiting embodiment, $R^1$ and $R^2$ each correspond to $R^3(OCH_2CH_2)_nO$, and each X is sulfur, and $R^1$ and $R^2$ are the same, thus forming an alkyl dithiophosphoric acid as described in U.S. Pat. No. 3,909,447, which is incorporated herein by reference in its entirety. Preparation of alkyl dithiophosphoric acids is discussed in U.S. Pat. No. 3,909,447, and some are commercially available. Compositions of that patent may be effective in this invention, and the full scope of those compositions described as within the scope of the claims of that patent may be selected for use in the present invention. Such compositions often also comprise isomers of the thiophosphorus compounds as well.

Alternatively or additionally, the phosphorus-based compound may be a thiophosphinic acid. These compounds correspond to FORMULA 1 wherein each of $R^1$ and $R^2$ is $R^3(OCH_2CH_2)_n$, with $R^1$ preferably but not necessarily being the same as $R^2$, one X (most preferably the X double bonded to the phosphorus) is sulfur and the other X is sulfur or oxygen (most preferably, sulfur), $R^3$ is an alkyl group of about 6 to about 18 carbon atoms and n is an integer from 0 to about 12. Preferred identities and ranges of the variables are as discussed hereinabove with respect to the alkyl dithiophosphoric acids. Thiophosphinic acids are known and certain forms are commercially available.

Yet another form of the thiophosphorus compounds is a thiophosphonic acid, corresponding to FORMULA 1 wherein $R^1$ is $R^3(OCH_2CH_2)_n$, $R^2$ is XH, one X (most preferably the X double bonded to the phosphorus) is sulfur and each other X is sulfur or oxygen (most preferably, sulfur), $R^3$ is an alkyl group of about 6 to about 18 carbon atoms and n is an integer from 0 to about 12. Again, preferred identities and ranges of the variables are as discussed with respect to the alkyl dithiophosphoric acids.

The salts and alkyl and aryl esters of any of such thiophosphorus compounds may also be employed, either in combination with the acids or in place of them. Exemplary of types of suitable salts are discussed in U.S. Pat. No. 3,909,447, which is incorporated herein by reference in its entirety. Although they are discussed therein solely with respect to the alkyl dithiophosphoric acid, equivalent salts may be formed with the other thiophosphorus compounds. The esters may be formed by reaction of any of the noted thiophosphorus compounds with an alcohol. Preferred alcohols have up to about 18, preferably up to about 12, carbon atoms. Thus, they are of the form R*OH, wherein R* is an alkyl or aryl group of up to about 18, preferably up to about 12, more carbon atoms than does the thiophosphorus compound from which they are derived.

The isomers of the thiophosphorus compounds are generally dimers. Often, as discussed in U.S. Pat. No. 3,909,447, they are formed inherently in the preparation of the thiophosphorus compounds. In a preferred embodiment, therefore, the corrosion inhibitor composition is a mixture of alkyl dithiophosphoric acid and isomers thereof in accordance with the teachings of U.S. Pat. No. 3,909,447, in addition to the sulfur-based constituent. However, as noted, the compositions of the invention need not include a mixture of the phosphorus-based compounds, but may include only one such compound, along with the sulfur-based and/or nitrogen-based constituent.

Generally, the isomers are of the formula

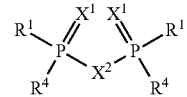

wherein $X^1$ represents sulfur, $X^2$ represents sulfur or oxygen, $R^1$ is as defined in previous formulas, and $R^4$ is the same as $R^1$ or corresponds to the formula $R^3(OCH_2CH_2)_n$. wherein $R^3$ is as defined above. In some non-limiting embodiments, it is desirable that $R^4$ is the same as $R^1$ and $X^1$ is sulfur. A mixture of isomers with alkyl dithiophosphoric acid, as described in U.S. Pat. No. 3,909,447, may also be selected for the phosphorus-based constituent.

Where a phosphate ester is chosen as all or part of a phosphorus-based constituent, in one non-limiting embodiment it conforms to the formula

FORMULA 9

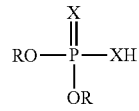

wherein X is independently sulfur or oxygen, and R is independently —H, —SH, —SR, —SSR, or C1-12 normal or partially or fully branched alkyl that is saturated or unsaturated. Examples of the phosphate esters include, for example, phosphate ester itself, thiophosphate ester, ethoxylated thiophosphate ester, combinations thereof, and the like.

The most effective amount of the corrosion inhibitor composition of the present invention to be used in accordance with this invention may vary, depending upon the local operating conditions and the particular hydrocarbon being processed. Thus, the temperature and other characteristics of the acid corrosion system would typically be considered in determining the amount of inhibitor composition to be used. Variations in the ratios of the components within each constituent may be made and may, in some cases, produce preferred results under different conditions and in different corrosion systems.

In general, where the operating temperatures and/or the acid concentrations are higher, a proportionately higher amount of the corrosion inhibitor composition will be required. It has been found that the concentration of the corrosion inhibitor composition may range from about 10 ppm to about 5,000 ppm or higher. It has also been found that it is preferable to add the inhibitor composition at a relatively high initial dosage rate, in one non-limiting embodiment from about 2,000 ppm to about 5,000 ppm, and to maintain this level for a relatively short period of time until the presence of the inhibitor induces the build-up of a corrosion protective coating on the metal surfaces. Once the protective coating is established, the dosage rate needed to maintain the protection may in some non-limiting embodiments be reduced to an operational range. Such operational range may be from about 10 to about 100 ppm, desirably from about 10 to about 50 ppm, and more desirably from about 10 to about 25 ppm, without substantial sacrifice of protection.

While the gas oil and other crude oil fractions often contain naphthenic acid which contributes to the corrosion problem which is particularly addressed by the present invention, the inhibitor compositions of the invention are useful in not only that part of a refinery handling these petroleum intermediates, but are also useful throughout an oil refinery in which acidic hydrocarbons are in contact with iron-containing metal surfaces.

The description hereinabove is intended to be general and is not intended to be inclusive of all possible embodiments of the invention. Similarly, the examples hereinbelow are provided to be illustrative only and are not intended to define or limit the invention in any way. Those skilled in the art will be fully aware that other embodiments within the scope of the claims will be apparent, from consideration of the specification and/or practice of the invention as disclosed herein. Such other embodiments may include selections of specific sulfur-based, nitrogen-based, and phosphorus-based compounds, and combinations of such compounds; proportions of such compounds; mixing and usage conditions, vessels, and protocols; hydrocarbon fluids; performance in inhibiting or controlling corrosion; and the like; and those skilled in the art will recognize that such may be varied within the scope of the appended claims hereto.

EXAMPLES

Example 1

A number of kettle tests were run. These tests were carried out in a resin vessel at a temperature of about 550° F. (~287° C.) in hydrocarbon fluids having acid numbers of about 4. The acid number was calculated based on the amount of a commercial grade of naphthenic acid with a nominal acid number. The vessel was heated with a heating mantle, which is controlled by a thermocouple and commercially-available temperature controller. Sparging with 1 percent hydrogen sulfide gas in argon introduced a constant level of sulfide. The sparge gas was first passed through a 100 mL graduated cylinder filled with water, and then through an empty 100 mL graduated cylinder. The second graduated cylinder was a trap to avoid backflow of hot liquids as the vessel cooled. Stirring at about 400 rpm with a paddle stirrer provided moderate agitation and velocity.

Corrosion rates were calculated based on the 20-hour weight loss of carbon steel coupons immersed in the hydrocarbon fluid. Results of the tests are shown in Table 1. In that table the "Inhibitor" column specifies whether no inhibitor was used ("Blank"); and where an inhibitor was used, whether it was: (1) a sulfur-based inhibitor as defined in the present invention, used alone (in this case, it is tropylene), denominated "Sulf-Inhib"; (2) a commercially-available phosphorus-based inhibitor, denominated as "Phos-Inhib" (not as defined in the present invention); (3) a thiophosphate inhibitor as defined in the present invention, denominated "TPE-Inhib"; or (4) a combination of the sulfur-based and thiophosphate inhibitors in the proportions shown, according to the present invention. "Weight" is shown in grams. "Mpy" refers to mils per year, which was the estimated annual weight loss based on the average loss resulting from each set of two coupons.

TABLE 1

| Inhibitor | Percent | Initial Weight | Final Weight | Weight Loss | Avg. Loss | Mpy | Avg. mpy |
|---|---|---|---|---|---|---|---|
| Blank* | n/a | 9.9507 | 9.9367 | 0.0140 | 0.0130 | 18.2642 | 16.9874 |
|  |  | 9.9778 | 9.9657 | 0.0121 |  | 15.7106 |  |
| Blank* | n/a | 10.0163 | 9.9932 | 0.0231 | 0.0195 | 29.9331 | 25.2456 |
|  |  | 9.9838 | 9.9679 | 0.0159 |  | 20.5580 |  |
| Blank* | n/a | 10.0385 | 10.0255 | 0.0130 | 0.0136 | 16.9225 | 17.6150 |
|  |  | 10.0427 | 10.0285 | 0.0142 |  | 18.3074 |  |
| Blank* | n/a | 10.0776 | 10.0635 | 0.0142 | 0.0122 | 18.3941 | 15.7540 |
|  |  | 10.0051 | 9.9950 | 0.0101 |  | 13.1139 |  |
| TPE-Inhib | 100 | 10.0636 | 10.0631 | 0.0005 | 0.0004 | 0.6492 | 0.6925 |
|  |  | 10.0515 | 10.0512 | 0.0003 |  | 0.7358 |  |
| Sulf-Inhib | 100 | 10.0753 | 10.0647 | 0.0106 | 0.0105 | 13.9198 | 13.6900 |
|  |  | 10.0792 | 10.0688 | 0.0104 |  | 13.4601 |  |
| Phos-Inhib* | 100 | 10.0676 | 10.0600 | 0.0077 | 0.0090 | 9.9977 | 11.6857 |
|  |  | 10.0798 | 10.0695 | 0.0103 |  | 13.3736 |  |

TABLE 1-continued

| Inhibitor | Percent | Initial Weight | Final Weight | Weight Loss | Avg. Loss | Mpy | Avg. mpy |
|---|---|---|---|---|---|---|---|
| Phos-Inhib* | 100 | 10.0285 | 10.0231 | 0.0054 | 0.0042 | 7.0114 | 5.4101 |
|  |  | 10.0733 | 10.0704 | 0.0029 |  | 3.8087 |  |
| Phos-Inhib* | 100 | 10.0592 | 10.0502 | 0.0090 | 0.0108 | 11.6856 | 14.0228 |
|  |  | 10.0146 | 10.0020 | 0.0126 |  | 16.3599 |  |
| TPE-Inhib/Sulf-Inhib | 50/50 | 10.0395 | 10.0379 | 0.0016 | 0.0022 | 2.2073 | 2.9431 |
|  |  | 10.0308 | 10.0280 | 0.0028 |  | 3.6788 |  |
| TPE-Inhib/Sulf-Inhib | 50/50 | 10.0396 | 10.0374 | 0.0022 | 0.0018 | 2.8998 | 2.3588 |
|  |  | 10.0334 | 10.0320 | 0.0014 |  | 1.8178 |  |
| TPE-Inhib/Sulf-Inhib | 75/25 | 10.0562 | 10.0534 | 0.0028 | 0.0028 | 3.5923 | 3.5274 |
|  |  | 10.0965 | 10.0938 | 0.0027 |  | 3.4624 |  |
| TPE-Inhib/Sulf-Inhib | 75/25 | 10.0228 | 10.0208 | 0.0020 | 0.0018 | 2.5968 | 2.3371 |
|  |  | 10.0948 | 10.0932 | 0.0016 |  | 2.0774 |  |
| TPE-Inhib/Sulf-Inhib | 25/75 | 10.0622 | 10.0590 | 0.0032 | 0.0035 | 2.8565 | 3.8087 |
|  |  | 10.0988 | 10.0951 | 0.0037 |  | 4.7608 |  |
| TPE-Inhib/Sulf-Inhib | 25/75 | 10.0192 | 10.0167 | 0.0025 | 0.0024 | 3.2893 | 3.0946 |
|  |  | 10.0755 | 10.0733 | 0.0022 |  | 2.8998 |  |
| TPE-Inhib/Sulf-Inhib | 25/75 | 10.0533 | 10.0514 | 0.0019 | 0.0026 | 2.4237 | 3.2893 |
|  |  | 9.9998 | 9.9966 | 0.0032 |  | 4.1549 |  |
| Blank | n/a | 10.0776 | 10.0635 | 0.0142 | 0.0122 | 18.3941 | 15.7540 |
|  |  | 10.0051 | 9.9950 | 0.0101 |  | 13.1139 |  |
| Sulf-Inhib | 75** | 10.0988 | 10.0868 | 0.0120 | 0.0115 | 15.5376 | 14.8668 |
|  |  | 10.0379 | 10.0269 | 0.0109 |  | 14.1959 |  |
| Sulf-Inhib | 50** | 9.9235 | 9.9135 | 0.0100 | 0.0101 | 12.9841 | 12.6595 |
|  |  | 10.0771 | 10.067 | 0.0101 |  | 12.3348 |  |
| Sulf-Inhib | 25** | 10.0658 | 10.0558 | 0.0100 | 0.0104 | 12.9408 | 13.4385 |
|  |  | 9.9847 | 9.9739 | 0.0107 |  | 13.9362 |  |
| Tropylene* | 25** | 10.0793 | 10.0692 | 0.0101 | 0.0103 | 13.1139 | 13.3087 |
|  |  | 10.0991 | 10.0887 | 0.0104 |  | 13.5034 |  |

*Not an example of the present invention.
**These represent the total amount of inhibitor, i.e., in comparison with the total amount used in tests recorded higher on Table 1.

The test results showed that comparable or near-comparable inhibition was achieved by the inventive compositions in comparison with those including only the commercially-available phosphorus-based inhibitor.

Example 2

Additional tests were run according to the method of Example 1 and at the same temperature (550° F., 287° C.). However, in this series of tests the amount of inhibition ("% Inhib." and "Avg. % Inhib.") occurring in each test was also calculated. Results are shown in Table 2.

TABLE 2

| Inhibitor | Percent | Wt. Loss | Avg. Loss | Mpy | Avg. mpy | % Inhib. | Avg. % Inhib. |
|---|---|---|---|---|---|---|---|
| Blank* | n/a | 0.0231 | 0.0195 | 19.9331 | 25.2456 | n/a | n/a |
|  |  | 0.0158 |  | 20.5580 |  |  |  |
| TPE-Inhib | 100 | 0.0005 | 0.0004 | 0.6492 | 0.6925 | 97.4293 | 97.9434 |
|  |  | 0.0003 |  | 0.7358 |  | 98.4576 |  |
| Sulf-Inhib | 100 | 0.0106 | 0.0105 | 13.9198 | 13.6900 | 45.5013 | 46.0154 |
|  |  | 0.0104 |  | 13.4601 |  | 46.5296 |  |
| Phos-Inhib* | 100 | 0.0077 | 0.0090 | 9.9977 | 11.6857 | 60.4113 | 53.7275 |
|  |  | 0.0103 |  | 13.3736 |  | 47.0437 |  |
| Phos-Inhib* | 100 | 0.0054 | 0.0042 | 7.0114 | 5.4101 | 72.2365 | 78.6632 |
|  |  | 0.0029 |  | 3.8087 |  | 85.0900 |  |
| Phos-Inhib* | 100 | 0.0090 | 0.0108 | 11.6856 | 14.0228 | 53.7275 | 44.4730 |
|  |  | 0.0126 |  | 16.3599 |  | 35.2185 |  |
| TPE-Inhib/Sulf-Inhib | 50/50 | 0.0016 | 0.0022 | 2.2073 | 2.9431 | 91.7738 | 88.6889 |
|  |  | 0.0028 |  | 3.6788 |  | 85.6041 |  |
| TPE-Inhib/Sulf-Inhib | 50/50 | 0.0022 | 0.0018 | 2.8998 | 2.3588 | 88.6889 | 90.7455 |
|  |  | 0.0014 |  | 1.8178 |  | 92.8021 |  |
| TPE-Inhib/Sulf-Inhib | 75/25 | 0.0028 | 0.0028 | 3.5923 | 3.5274 | 85.6041 | 85.8612 |
|  |  | 0.0027 |  | 3.4624 |  | 86.1183 |  |
| TPE-Inhib/Sulf-Inhib | 75/25 | 0.0020 | 0.0018 | 2.5968 | 2.3371 | 89.7172 | 90.7455 |
|  |  | 0.0016 |  | 2.0774 |  | 91.7738 |  |
| TPE-Inhib/Sulf-Inhib | 25/75 | 0.0032 | 0.0035 | 4.1549 | 4.4579 | 83.5486 | 82.2622 |
|  |  | 0.0037 |  | 4.7608 |  | 80.9769 |  |
| TPE-Inhib/Sulf-Inhib | 25/75 | 0.0025 | 0.0024 | 3.2893 | 3.0946 | 87.1465 | 87.9177 |
|  |  | 0.0022 |  | 2.8998 |  | 88.6889 |  |
| TPE-Inhib/Sulf-Inhib | 25/75 | 0.0019 | 0.0026 | 2.4237 | 3.2893 | 90.2314 | 86.8895 |
|  |  | 0.0032 |  | 4.1549 |  | 83.5476 |  |

*Not an example of the present invention.

Example 3

Gas oil obtained from a refining company processing high acid crude oil, having a TAN of from about 4.5 to about 5.0, was kettle-tested according to the protocol of Example 1, except that the temperature was about 600° F. (−315° C.). Inhibitors were added to the gas oil in the amounts shown, and the mpy was averaged over 20 hours, with each value given representing three coupons tested. Results are shown in Table 3.

TABLE 3

| Inhibitor | Amount in ppm | Avg. mpy, 3 coupons per test |
| --- | --- | --- |
| Blank* | n/a | 33, 37.3, 34.4, 33.2 |
| TPE-Inhib | 2600 | 2.6, 2.6, 4.2 |
| Sulf-Inhib | 2600 | 14, 25 |
| Sulf-Inhib + TPE-Inhib | 1300 + 1300 | 5, 4.7, 3.7, 8.3, 5.7, 4.5 |
| Sulf-Inhib + TPE-Inhib | 860 + 1740 | 4.1, 6.3, 8.8, 5.7, 4.5 |
| Sulf-Inhib + TPE-Inhib | 1740 + 860 | 2.4, 3.8, 6.5, 6 |
| Sulf-Inhib + TPE-Inhib | 1950 + 650 | 3.5, 3.9, 4.9, 4.5, 9.9, 9.5 |
| Sulf-Inhib + TPE-Inhib | 650 + 1950 | 5.4, 5.5, 6.6, 7.5 |
| Sulf-Inhib + TPE-Inhib | 2340 + 260 | 5.0, 6.7, 42** |
| TPE-Inhib | 1700 | 8.9, 7.8 |
| TPE-Inhib | 1300 | 5.2, 3.9 |
| TPE-Inhib | 900 | 5.8, 11.4 |

*Not an example of the invention.
**Anomalous result leads to presumption of experimental error.

We claim:

1. A method for inhibiting naphthenic acid corrosion of metals in hydrocarbon fluids comprising adding to a non-aqueous hydrocarbon fluid, in an amount sufficient to inhibit corrosion therein, a corrosion inhibitor composition comprising:

a phosphorus-based constituent comprising at least one compound selected from the group consisting of:

a. thiophosphorus compounds of the formula

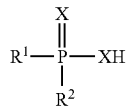

wherein $R^1$ is $R^3(OCH_2CH_2)_n$ or $R^3(OCH_2CH_2)_nO$; $R^2$ is the same as $R^1$ or XH, each X being independently sulfur or oxygen; provided however that at least one X is sulfur; $R^3$ is an alkyl group of from about 6 to about 18 carbon atoms; and n is an integer of from about 0 to about 12;

b. salts of the thiophosphorus compounds;

c. alkyl and aryl esters of the thiophosphorus compounds; and d. isomers of the thiophosphorus compounds; and e. phosphate ester compounds;

a sulfur-based constituent that is 1,2,4-dithiazole-3-thione; and a nitrogen-based constituent selected from the group consisting of acridine, phenanthridine, octahydrophenanthridine, and combinations thereof;

provided that the phosphorus-based constituent is present in minor portion.

2. The method of claim 1 wherein the temperature of the hydrocarbon fluid is from about 175° C. to 400° C.

3. The method of claim 1 wherein the amount of the inhibitor composition is from about 10 ppm to about 5,000 ppm.

4. A composition for inhibiting or controlling naphthenic acid induced corrosion in a non-aqueous hydrocarbon fluid comprising:

a phosphorus-based constituent comprising at least one compound selected from the group consisting of:

a. thiophosphorus compounds of the formula

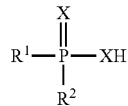

wherein $R^1$ is $R^3(OCH_2CH_2)_n$ or $R^3(OCH_2CH_2)_nO$; $R^2$ is the same as $R^1$ or XH, each X being independently sulfur or oxygen; provided however that at least one X is sulfur; $R^3$ is an alkyl group of from about 6 to about 18 carbon atoms; and n is an integer of from about 0 to about 12;

b. salts of the thiophosphorus compounds;

c. alkyl and aryl esters of the thiophosphorus compounds; and d. isomers of the thiophosphorus compounds; and e. phosphate ester compounds;

a sulfur-based constituent that is 1,2,4-dithiazole-3-thione; and a nitrogen-based constituent comprising at least one compound conforming to one of the following formulas:

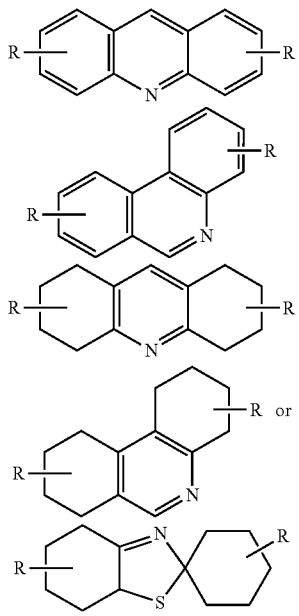

wherein R is —H, —SH, —SR, —SSR, or C1-C12 normal or partially or fully branched alkyl that is saturated or unsaturated;

provided that the phosphorus-based constituent is present in minor portion;

where the composition is capable of inhibiting or controlling naphthenic acid induced corrosion in a non-aqueous hydrocarbon fluid.

5. The composition of claim 4 wherein the minor portion is no more than about 40 percent by weight of the composition.

6. The composition of claim 5 wherein the minor portion is no more than about 30 percent by weight of the composition.

7. The composition of claim 4 wherein the nitrogen-based constituent is selected from the group consisting of acridine, phenanthridine, octahydrophenanthridine, 1,3-thiazole, and combinations thereof.

8. A composition for inhibiting or controlling naphthenic acid induced corrosion in a non-aqueous hydrocarbon fluid where the composition comprises:
- a sulfur-based constituent that is 1,2,4-dithiazole-3-thione; and
- a nitrogen-based constituent selected from the group consisting of acridine, phenanthridine, octahydrophenanthridine, 1,3-thiazole, and combinations thereof;
- wherein the composition is present in major portion and where the composition is capable of inhibiting or controlling naphthenic acid induced corrosion in a non-aqueous hydrocarbon fluid.

* * * * *